US009249185B2

(12) United States Patent
Bang et al.

(10) Patent No.: US 9,249,185 B2
(45) Date of Patent: Feb. 2, 2016

(54) PEPTIDES FOR PROMOTING ANGIOGENESIS AND AN USE THEREOF

(75) Inventors: Sa Ik Bang, Seoul (KR); Juah Son, Seoul (KR); Sang Yoon Kim, Seoul (KR); Jeong Min Park, Suwon-si (KR); Yoo Rim Park, Seoul (KR); Ha Rum Lee, Seoul (KR); Sun Young Yoon, Seoul (KR); Dae Ho Cho, Seoul (KR)

(73) Assignees: INDUSTRY-ACADEMIC COOPERATION FOUNDATION, SOOKMYUNG WOMEN'S UNIVERSITY, Seoul (KR); IL-YANG PHARM. CO., LTD, Gyeonggi-do (KR); SAMSUNG LIFE WELFARE FOUNDATION, Seoul (KR)

( * ) Notice: Subject to any disclaimer, the term of this patent is extended or adjusted under 35 U.S.C. 154(b) by 0 days.

(21) Appl. No.: 13/637,604

(22) PCT Filed: Mar. 25, 2011

(86) PCT No.: PCT/KR2011/002080
§ 371 (c)(1),
(2), (4) Date: Dec. 17, 2012

(87) PCT Pub. No.: WO2011/119008
PCT Pub. Date: Sep. 29, 2011

(65) Prior Publication Data
US 2013/0085108 A1    Apr. 4, 2013

(30) Foreign Application Priority Data

Mar. 26, 2010 (KR) .................. 10-2010-0027373

(51) Int. Cl.
C07K 7/06     (2006.01)
C07K 5/103    (2006.01)
A61L 27/22    (2006.01)
A61K 38/00    (2006.01)

(52) U.S. Cl.
CPC ............... *C07K 7/06* (2013.01); *A61L 27/227* (2013.01); *C07K 5/1008* (2013.01); *A61K 38/00* (2013.01)

(58) Field of Classification Search
CPC ........ A61K 38/00; A61K 9/08; A61L 27/227; A61L 27/00; C07K 5/1008; C07K 7/06; A63B 69/36
See application file for complete search history.

(56) References Cited

U.S. PATENT DOCUMENTS 4,395,404 A *  7/1983  Low et al. ............... 514/12.9
5,073,492 A    12/1991 Chen et al.
2004/0052810 A1  3/2004  Nesbit et al.

FOREIGN PATENT DOCUMENTS

| EP | 0 506 477 A1 | 9/1992 | | |
|---|---|---|---|---|
| WO | WO 88/03151 | 5/1988 | | |
| WO | WO 0006190 A1 * | 2/2000 | ............. | A61K 38/22 |
| WO | WO01/05812 A2 | 1/2001 | | |
| WO | WO02051438 | 7/2002 | | |
| WO | 2004/074460 A2 | 9/2004 | | |
| WO | WO2005/094865 A1 | 10/2005 | | |
| WO | WO 2009034041 A2 * | 3/2009 | ........... | A61K 39/005 |

OTHER PUBLICATIONS

A. Raiter, Angiogenic Peptides Improve Blood Flow and Promote Capillary Growth in a Diabetic and Ischaemic Mouse Model, Eur J Vasc Endovasc Surg, 2010, 40, 381-388.*
Martin C. Robson, Sequential Cytokine Therapy for Pressure Ulcers: Clinical and Mechanistic Response, Annals of Surgery, vol. 231, No. 4, 600-611, 2000.*
UniProt Protein Database, Salivary gland 7-like protein, Protein Accession No. Q8WR31, pp. 1-2, accessed Jul. 18, 2014.*
UniProt Protein Databse, Protein Acession Q2W7B4, Histone acetyltransferase HPA2 and related acetyltransferase, pp. 1-5, accessed on May 11, 2015.*
XP_416677 in NCBI data base Predicted: similar to ATP-binding Cassette transporter 13 [Gallus gallus]; downloaded Aug. 26, 2013, http://www.ncbi.nlm.nih.gov/protein/118083747?sat=15 &satkey=2455417.
International Search Report, PCT/KR2011/002080, dated Feb. 2, 2012, 4 pages.
Supplementary European Search Report, EP11759757, Sep. 16, 2013.
Lahdesmaki, P. et al., "Characterization of Two Synaptosomal Peptides in Calf Brain", Acta Chemica Scandinavica, B34:343-348 (1980).
Mu, H. et al., "Adipkine resistin promotes in vitro angiogenesis of human endothelial cells", Cardiovascular Research, 70:146-157 (2006).
NCBI Reference Sequence ZP_01462441.1, tRNA pseudouridine synthase A [Stigmatella aurantiaca DW4/3-1] Protein, retrieved Feb. 21, 2013.

(Continued)

*Primary Examiner* — James H Alstrum Acevedo
*Assistant Examiner* — Erinne Dabkowski
(74) *Attorney, Agent, or Firm* — Lathrop & Gage LLP; Brian C. Trinque, Esq.; Andrew T. Wilkins, Esq.

(57) ABSTRACT

The present invention relates to a peptide promoting angiogenesis and novel use thereof. More particularly, the invention relates to peptides promoting angiogenesis, and the use of the peptide for promoting angiogenesis and preventing or treating angiogenesis-related disease. The peptide of the present invention have an excellent effect on promoting angiogenesis. Accordingly, it is useful for preventing or treating angiogenesis-related disease and for preparing regeneration of skin flap, wound and burn healing, implantation of artificial-skin and preparation of blood vessels for transplantation.

3 Claims, 2 Drawing Sheets

(56) References Cited

OTHER PUBLICATIONS

Sequence UPI000146D827, UniProt Database, Ref. XP-002701545, www.uniprot.org, retrieved Jul. 8, 2013.

Hanahan, D., "Signaling Vascular Morphogenesis and Maintenance", Science, 277:48-50 (1997).

Hogan, B.L.M. et al., "Molecular Mechanisms of Tubulogenesis", Nature Reviews Genetics, 3:513-523 (2002).

Bussolino, F. et al., "Molecular mechanisms of blood vessel formation", Trends in Biochemical Science, 22:251-256 (1997).

Ferrara, N. et al. "The Biology of Vascular Endothelial Growth Factor", Endocrine Reviews, 18(1):4-25 (1997).

Breier, G. et al., "Expression of vascular endothelial growth factor during embryonic angiogenesis and endothelial cell differentiation", Development 114:521-532 (1992).

Binetruy-Tourniere, R. et al., "Identification of a peptide blocking vascular endothelial grown factor (VEGF)-mediated angiogenesis", The EMBO Journal, 19(7):1525-1533 (2000).

Lu, D. et al., "Tailoring in Vitro Selection for a Picomolar Affinity Human Antibody Directed against Vascular Endothelial Growth Factor Receptor 2 for Enhanced Neutralizing Activity", Journal of Biological Chemistry, 278 (44):43496-43507 (2003).

Database Geneseq [online] (Jun. 15, 2007) "Caenorhabditis elegans caronte protein," Accession No. ADR47513.

Database Geneseq [online] (May 14, 2009) "Anopheles gambiae salivary gland 7-like protein," Accession No. AWl98798.

Extended European Search Report corresponding to European Patent Application No. 15172588.4, dated Sep. 30, 2015.

\* cited by examiner

PEPTIDES FOR PROMOTING ANGIOGENESIS AND AN USE THEREOF

RELATED APPLICATIONS

The present application claims the benefit of priority of International Application No. PCT/KR2011/002080 filed Mar. 25, 2011, which claims priority to Korean Patent Application No. 10-2010-0027373, filed Mar. 26, 2010. The entire contents of each of the above documents are incorporated herein by reference.

The present invention relates to peptides for promoting angiogenesis and an use thereof. More particularly, the invention relates to peptides promoting angiogenesis, and the use of the peptide for promoting angiogenesis and preventing or treating angiogenesis-related disease.

BACKGROUND ART

Development of a vascular supply is a fundamental requirement for many physiological and pathological processes. Actively growing tissues such as embryos and tumors require adequate blood supply. They satisfy this need by producing pro-angiogenic factors, which promote new blood vessel formation via a process called angiogenesis. Vascular tube formation is a complex but orderly biological event involving all or many of the following steps: a) endothelial cells (ECs) proliferate from existing ECs or differentiate from progenitor cells; b) ECs migrate and coalesce to form cord-like structures; c) vascular cords then undergo tubulogenesis to form vessels with a central lumen; d) existing cords or vessels send out sprouts to form secondary vessels; e) primitive vascular plexus undergo further remodeling and reshaping; and f) peri-endothelial cells are recruited to encase the endothelial tubes, providing maintenance and modulatory functions to the vessels; such cells including pericytes for small capillaries, smooth muscle cells for larger vessels, and myocardial cells in the heart (Hanahan, D., *Science,* 1997, 277, 48; Hogan, B. L. & Kolodziej, P. A. *Nature Reviews Genetics,* 2002, 3, 513).

The development of the blood vessels is strictly controlled. Up to the present, a large number of secretory factors produced by peripheral cells are known to regulate differentiation, proliferation and migration of ECs and coalescence into cord-like structures. The angiogenesis-promoting factors reported thus far can be largely classified into a few groups. They are mostly growth-inducing factors that induce cellular growth, cytokines having immune activity, hormones, or lipid products (Bussolino F et al., *Trends Biochem. Sci.,* 22(7), pp. 251-256, 1997).

Vascular endothelial growth factor (VEGF) has been identified as the key factor involved in stimulating angiogenesis and in inducing vascular permeability (Ferrara et al., *Endocr. Rev.* 18: 4-25, 1997). A form of murine VEGF gene was identified and the expression pattern was analyzed during its embryogenesis. Continued expression of VEGF was observed in spear-shaped epithelial cells neighboring the endothelium, e.g. the choroid plexus and the glomerulus of the kidney. These data correspond to the role of VEGF as a multifunctional factor regulating the growth and differentiation of the ECs (Breier, G. et al., *Development,* 1992, 114, 521).

VEGF is involved in angiogenesis in all connective tissues (e.g., lungs, heart, placenta and solid tumors) (Binetruy-Tourniere et al., *EMBO J.* 2000, 19, 1525). For example, VEGF is involved in growth of solid tumor and metastasis by stimulating tumor-related angiogenesis (Lu et al., *J. Biol. Chem.* 2003, 278, 43496). Also, since the VEGF expression is essential in the restoration of connective tissues, use of the VEGF for the restoration of the connective tissues was proposed.

Actually, Chen et al. disclosed a method for synergistically enhancing endothelial cell growth in an appropriate environment therefor which comprises adding to the environment, VEGF, effectors and serum-derived factor in U.S. Pat. No. 5,073,492 (Dec. 17, 1991). Also, vascular endothelial cell growth factor C subunit DNA is prepared by polymerase chain reaction techniques. The DNA encodes a protein that may exist as either a heterodimer or homodimer. The protein is a mammalian vascular endothelial cell mitogen and, as described in European Patent Application No. 92302750.2 (Sep. 30, 1992) is known to be useful for the promotion of vascular development and repair as it is.

Despite the advancement regarding VEGF, when subjected to animal experiments, it fails to pass through the blood barrier due to its large molecular size like other proteins and is eliminated in short time due to short half-life. Although studies are actively carried out to find out the important EC-specific genes involved in angiogenesis and thus to treat various angiogenesis-related diseases, there is no substantial result as yet.

DISCLOSURE

Technical Problem

The inventors of the present invention have studied to find out peptides that can replace vascular endothelial growth factor (VEGF). Through synthesis of several novel peptides followed by repeated substitution, addition and deletion of their residues and screening of effective derivatives, they have synthesized a novel peptide providing an angiogenesis-promoting effect.

The present invention is directed to providing an isolated peptide having an amino acid sequence represented by the general formula (I):

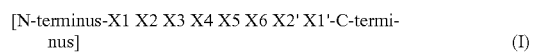

[N-terminus-X1 X2 X3 X4 X5 X6 X2' X1'-C-terminus]     (I)

wherein X1 and X1' is each independently non-existence or a basic amino acid, X2 and X2' is each independently non-existence or a polar amino acid, X3 is alanine, X4 is glycine, X5 is a charged amino acid, and X6 is serine.

The present invention is also directed to providing a use of the peptide for promoting angiogenesis for preparing of regeneration of skin flap, wound and burn healing, implantation of artificial skin and preparation of blood vessels for transplantation.

The present invention is also directed to providing a use of the peptide for prevention or treatment of angiogenesis-related diseases selected from a group consisting of diabetic retinopathy, retinopathy of prematurity, age-related macular degeneration, glaucoma, diabetic foot ulcer, pulmonary hypertension, ischemic cardiomyopathy, ischemic brain disease, heart failure, acute posterior ischemia, bedsore, chronic ulcer, baldness or hair graying, obesity-related cardiovascular disease, and ischemia.

Technical Solution

To achieve the object, the present invention provides an isolated peptide having an amino acid sequence represented by the general formula (I):

[N-terminus-X1 X2 X3 X4 X5 X6 X2' X1'-C-terminus]   (I)

wherein X1 and X1' is each independently non-existence or a basic amino acid, X2 and X2' is each independently non-existence or a polar amino acid, X3 is alanine, X4 is glycine, X5 is a charged amino acid, and X6 is serine.

To achieve another object, the present invention provides a composition for promoting angiogenesis comprising the peptide as an active ingredient.

To achieve another object, the present invention provides a pharmaceutical composition for prevention or treatment of angiogenesis-related diseases selected from a group consisting of diabetic retinopathy, retinopathy of prematurity, age-related macular degeneration, glaucoma, diabetic foot ulcer, pulmonary hypertension, ischemic cardiomyopathy, ischemic brain disease, heart failure, acute posterior ischemia, bedsore, chronic ulcer, baldness or hair graying, obesity-related cardiovascular disease, and ischemia comprising the peptide as an active ingredient.

To achieve another object, the present invention provides a peptide selected from a group consisting of the peptides of the present invention that is used for treatment reagents or diagnostic reagents.

To achieve another object, the present invention provides use of the peptide of the present invention for preparing reagents for promoting angiogenesis.

To achieve another object, the present invention provides a method for promoting angiogenesis by administering an effective amount of the peptide of the present invention to subject in need.

To achieve another object, the present invention provides use of the peptide of the present invention for preparing a reagent for prevention or treatment of angiogenesis-related diseases selected from a group consisting of diabetic retinopathy, retinopathy of prematurity, age-related macular degeneration, glaucoma, diabetic foot ulcer, pulmonary hypertension, ischemic cardiomyopathy, ischemic brain disease, heart failure, acute posterior ischemia, bedsore, chronic ulcer, baldness or hair graying, obesity-related cardiovascular disease, and ischemia.

To achieve another object, the present invention provides a method for prevention or treatment of angiogenesis-related diseases selected from a group consisting of diabetic retinopathy, retinopathy of prematurity, age-related macular degeneration, glaucoma, diabetic foot ulcer, pulmonary hypertension, ischemic cardiomyopathy, ischemic brain disease, heart failure, acute posterior ischemia, bedsore, chronic ulcer, baldness or hair graying, obesity-related cardiovascular disease, and ischemia by administering an effective amount of the peptide of the present invention to subject in need.

Hereafter, the present invention will be described in more detail.

The amino acids used herein are mentioned as follows according to IUPAC-IUB nomenclature:

Arginine: R,
Lysine: K,
Glutamix acid: E,
Threonine: T,
Glutamine: Q,
Glycine: G,
Alanine: A,
Leucine: L,
Phenylalanine: F,
Tyrosine: Y,
Histideine: H
Aspartic acid: D
Serine: S
Asparagine: N
Cysteine: C
Proline: P
Isoleucine: I
Methionine: M
Tryptophan: W
Valine: V The present invention provides a peptide having an isolated peptide having an amino acid sequence represented by the general formula (I):

[N-terminus-X1 X2 X3 X4 X5 X6 X2' X1'-C-terminus]   (I)

An isolated peptide of the present invention having an amino acid sequence represented by the general formula (I) is characterized as follows; X1 and X1' is each independently non-existence or a basic amino acid, X2 and X2' is each independently non-existence or a polar amino acid, X3 is alanine, X4 is glycine, X5 is a charged amino acid, and X6 is serine.

The peptide of the present invention has a basic structure of alanine-glycine-charged amino acid-serine and may further include basic amino acids and/or polar amino acids at both terminals.

The angiogenesis-promoting effect of the peptide having such a structure is known for the first time in the present invention.

Preferably, the basic amino acid may be arginine, histidine or lysine. The polar amino acid may be any polar amino acid. Preferably, it may be serine, threonine, asparagine or glutamine. The charged amino acid may be either an acidic amino acid or a basic amino acid. Preferably, it may be arginine, histidine, lysine, aspartic acid or glutamic acid.

Also, the peptide of the present invention may be a peptide further having proline at the N-terminus of the general formula (I).

The peptide of the present invention may be any one having an amino acid sequence represented by the general formula (I). Preferably, it may be a peptide having an amino acid sequence selected from a group consisting of SEQ ID NOs. 1 to 7.

The peptide of the present invention exhibits an angiogenesis-promoting effect. Although the length is not particularly limited as long as it includes an amino acid sequence represented by the general formula (I), but preferably, it may comprise an amino acid sequence represented by the general formula (I) and consists of 4 to 50 amino acids, more preferably 4 to 30 amino acids. More preferably, it may be a peptide having amino acid sequence represented by the general formula (I). Most preferably, the peptide of the present invention may be a peptide having an amino acid sequence selected from the group consisting of SEQ ID NOs. 1 to 7.

Also, the peptide of the present invention may be a peptide the C-terminus of which is amidated. In order to protect the peptide from proteases and increase stability in vivo, the N-terminus and the C-terminus are modified or protected with various protecting groups. That is to say, the C-terminus of the peptide may be modified in order to improve stability. The modification is not specially limited, but preferably the modification may be by hydroxyl (—OH) or amino (—NH$_2$) group. The amidation of the C-terminus means that the C-terminus of the peptide is modified with the amino (—NH$_2$) group.

Also, the N-terminus of the peptide may be modified in order to improve stability. The modification is not specially limited, but preferably the modification may be by a group selected from the group consisting of acetyl, fluorenylmethoxycarbonyl (Fmoc), formyl, palmitoyl, myristyl, stearyl and polyethylene glycol (PEG).

The peptide of the present invention may be prepared according to a method well known in the art. For example, it may be synthesized using an automated peptide synthesizer or it may be produced by a genetic modification technique. For instance, after producing a fusion gene encoding a fusion protein comprising a fusion partner and the peptide of the present invention through genetic modification, transfecting a host microorganism with the fusion gene, and expressing the fusion protein in the host microorganism, the peptide of the present invention may be cleaved and isolated from the fusion protein using an adequate protease or compound. For this end, a DNA sequence coding for an amino acid residue that can be cleaved by a protease such as factor Xa or enterokinase or a compound such as CNBr or hydroxylamine may be inserted between the fusion partner and the gene for the peptide of the present invention. For example, in order to provide a site cleaved by CNBr, a restriction site including armethionine codon with a matching reading frame (e.g., AflIII, BsmI, BspHI, BspLU11I, NcoI, NdeI, NsiI, Ppu10I, SphI or StyI) or its isoschizomer site is inserted at the 3'-terminus of the fusion partner to be cut by the restriction enzyme. And, a restriction site connected to the reading frame may be inserted at the 5'-terminus of the gene for the peptide of the present invention, which is cut by the enzyme to connect the fusion partner with the gene for the peptide of the present invention. For another example, in order to provide a site cleaved by hydroxylamine, a DNA sequence capable of encoding asparagine-glycine may be inserted between the fusion partner gene and the gene for the peptide of the present invention. For example, when the two genes are fused, a restriction site including an asparagine codon with a matching reading frame or its isoschizomer site may be inserted at the 3'-terminus of the fusion partner to be cut by the restriction enzyme, thus forming a terminus compatible to the enzyme or a blunt end. And, a restriction site including a glycine codon and connected to the reading frame may be inserted at the 5'-terminus of the gene for the peptide of the present invention, which is then cut by the restriction enzyme to connect the fusion partner gene with the gene for the peptide of the present invention. The gene construct according to the present invention may be inserted into commonly employed expression vectors, e.g. plasmid, viruses, or vehicles allowing insertion or incorporation of structural genes for cloning into host cells.

In an example of the present invention, peptides having amino acid sequences of SEQ ID NOs. 1 to 7 were synthesized using an automated peptide synthesizer and then isolated by C18 reversed-phase high-performance liquid chromatography.

The peptide of the present invention has an effect of promoting angiogenesis in human or animals. The angiogenesis-promoting effect of the peptide having the amino acid sequence of the present invention was first identified in the present invention.

The angiogenesis-promoting effect was demonstrated through an experiment using human umbilical vein endothelial cells (HUVECs).

In an example of the present invention, it was tested whether treatment of HUVECs with the peptide of the present invention promotes proliferation of the HUVECs. As a result, it was confirmed that the treatment with the peptide of the present invention promotes the proliferation of the HUVECs (Example 2).

In another example of the present invention, the effect of the peptide of the present invention on migration of HUVECs was investigated. After placing the peptide of the present invention at the bottom portion of a chamber with a polycarbonate filter having pores therebelow and adding HUVECs to the upper portion of the chamber, the number of cells that migrated to the bottom portion were counted and compared with the control group after incubation. As a result, it was confirmed that the peptide of the present invention promotes the migration of the HUVECs (Example 3).

In another example of the present invention, the effect of the peptide of the present invention on tube formation of HUVECs was investigated. After applying and hardening Matrigel on a plate, a mixture of the peptide of the present invention and HUVECs in a buffer was added and it was observed whether the HUVECs form tubes in the Matrigel. As a result, it was confirmed that the peptide of the present invention promotes the tube formation of the HUVECs (Example 4).

In another example of the present invention, in vivo Matrigel plug assay was performed to measure the angiogenesis-promoting ability of the peptide of the present invention. Following subcutaneous injection of a mixture of the peptide of the present invention with Matrigel to a mouse, Matrigel plug was taken out after 1 week and the degree of blood vessel formation was quantified. As a result, it was confirmed that the injection of the peptide of the present invention exhibited remarkably superior blood vessel formation as compared to the control group (Example 5).

As such, the peptide of the present invention promotes angiogenesis by proliferation, migration and differentiation of vascular cells. Accordingly, the present invention provides a composition for promotion of angiogenesis comprising the peptide of the present invention as an active ingredient. In addition, the present invention provides a peptide for treatment reagents and diagnostic reagents. Also, the present invention provides use of the peptide of the present invention for preparing a reagent for promoting angiogenesis. Also, the present invention provides a method for promoting angiogenesis by administering an effective amount of the peptide of the present invention to a subject in need.

Also, the present invention provides a pharmaceutical composition for prevention or treatment of angiogenesis-related diseases comprising the peptide of the present invention as an active ingredient. Also, the present invention provides use of the peptide for preparing a reagent for prevention or treatment of angiogenesis-related diseases selected from a group consisting of diabetic retinopathy, retinopathy of prematurity, age-related macular degeneration, glaucoma, diabetic foot ulcer, pulmonary hypertension, ischemic cardiomyopathy, ischemic brain disease, heart failure, acute posterior ischemia, bedsore, chronic ulcer, baldness or hair graying, obesity-related cardiovascular disease, and ischemia. Also, the present invention provides a method for prevention or treatment of angiogenesis-related diseases selected from a group consisting of diabetic retinopathy, retinopathy of prematurity, age-related macular degeneration, glaucoma, diabetic foot ulcer, pulmonary hypertension, ischemic cardiomyopathy, ischemic brain disease, heart failure, acute posterior ischemia, bedsore, chronic ulcer, baldness or hair graying, obesity-related cardiovascular disease, and ischemia by administering an effective amount of the peptide of the present invention to subject in need.

The present invention provides a composition comprising the peptide of the present invention as an effective ingredient. The composition of the present invention may be administered in combination with another biologically active agent, e.g. a biologically active compound, peptide, etc. The composition of the present invention may further comprise cells capable of differentiating into endothelial cells (ECs). preferably, the cells capable of differentiating into ECs may be embryonic stem cells, mesenchymal stem cells or hematopoietic stem cells.

The composition for promoting angiogenesis of the present invention may be used preferably for regeneration of skin flap, wound and burn healing, implantation of artificial skin, or preparation of blood vessels for transplantation, although not limited thereto. The vascular disease refers to a disease occurring from or aggravated by insufficient blood or oxygen supply because of anomalies in the blood vessels due to various causes. Preferably, non-limiting examples may include diabetic retinopathy, retinopathy of prematurity, age-related macular degeneration, glaucoma, diabetic foot ulcer, pulmonary hypertension, ischemic cardiomyopathy, ischemic brain disease, heart failure, acute posterior ischemia, bedsore, chronic ulcer, baldness or hair graying, obesity-related cardiovascular diseases, and ischemia.

Cardiovascular diseases such as myocardial infarction, angina, etc. are caused by obstruction or narrowing of the blood vessels. Insufficient supply of oxygen and nutrients through bloodstream leads to dysfunction of tissues and organs. If such vascular dysfunction occurs at the cardiac muscle, the heart stops beating, causing myocardial infarction or angina. If it occurs at the end of hands or feet, it leads to ischemic limb disease. In this case, the patient has to take psychoactive analgesic because of extreme pain. In severe cases, it ends in amputation or death.

Ischemic heart failure is caused by oxygen insufficiency resulting from reduced blood supply due to obstruction or narrowing of the blood vessels.

Diabetic neuropathy (foot ulcer) is the most common complication of diabetes mellitus, occurring in 50% or more of diabetic patients. High levels of blood sugar in the blood vessels of the diabetic patient cause functional anomalies of cells, leading to death of capillaries and nerve cells of the foot.

Diabetic retinopathy is caused by lesions on the capillary walls (thickening of the basement membrane, reduction in cells of the vascular walls, and excessive proliferation of ECs) caused by diabetes, leading to narrowing and occlusion of the capillaries and insufficient circulation to retinal microvessels.

A wound refers to an injury of the skin tissue such as surgical incision, ulcer of the digestive tract, burn, laceration and skin ulcer (e.g., bedsore). Usually, treatment of the wound involves first aid and waiting until the wound heals on its own, which takes a long time. In general, wound healing is influenced by the proliferation of cells and the formation of new connective or epithelial tissues resulting therefrom. For wound healing, promoting or stimulating proliferation and differentiation of cells is effective.

Baldness is caused by various reasons, but it is known that sufficient supply of nutrients to the hair roots from the nearby blood vessels is helpful in preventing and reversing hair loss.

The above-described diseases occur from or are aggravated by insufficient blood or oxygen supply because of anomalies in the blood vessels due to various causes, and may be improved by blood vessel implantation or vascular bypass. Accordingly, the composition comprising the peptide of the present invention as an effective ingredient may be used for angiogenesis or preparation of blood vessels for transplantation so as to improve or treat these diseases.

A pharmaceutical composition of the present invention may comprise a peptide of the present invention alone or further with one or more pharmaceutically acceptable carriers, excipients or diluents. A pharmaceutically acceptable carrier, for example, carriers for the parenteral or oral preparations may be included. The carriers for the parenteral preparations may comprise lactose, starch, cellulose derivatives, magnesium stearate, stearic acid. In addition, the carriers for the parenteral preparations may comprise water, oil, saline, aqueous glucose and glycol, and stabilizers and preservatives. The example of the stabilizers may be an antioxidant such as sodium hydrogen sulfite, sodium sulfite, and ascorbic acid. The example of the preservatives may be benzalkonium chloride, methyl- or prophyl-paraben, and chlorobutanol. The list of pharmaceutically acceptable carriers are disclosed in Remington Pharmaceutical Sciences, 19th ed., Mack Publishing Company, Easton, Pa., 1995.

A pharmaceutical composition of the present invention may be administered to mammals including human beings by any routes. For example, it may be administered parenterally or orally. For parenteral administration, but not limited thereto, it may be administered parenterally, by intravenous, intramuscular, intraarterial, intramarrow, subdural, intracardiac, intracutaneous, subcutaneous, intraperitoneal, intranasal, gastrointestinal tracts, parenteral, sublingual or rectum. For local administration, but not limited thereto, it comprise creams, ointments, gels and transdermal patches.

A pharmaceutical composition of the present invention may be prepared in the form of oral preparation or parenteral preparation according to the described above.

In case of the formulation for oral administration, the composition of the present invention may be formulated into powders, granules, tablets, pills, and sugar-coated tablets, capsules, liquids, gels, syrups, slurries, and emulsions by using the method known in the art. For example, preparations for oral administration may be harvested in the form of tablets or sugar-coated tablets by mixing an effective component with a solid excipient, grinding, and adding appropriate supplemental agents, then manufacturing a form of granular mixture. For examples of appropriate excipient, it may comprise sugars comprising lactose, dextrose, sucrose, sorbitol, mannitol, xylitol, erythritol and maltitol, starches comprising corn starch, wheat starch, rice starch and potato starch, celluloses comprising cellulose, methyl cellulose, sodium carboxymethylcellulose and hydroxypropylmethylcellulose, and fillers comprising gelatin and polyvinylpyrrolidone. And, if desired, it may comprise cross-linked polyvinylpyrrolidone, agar, alginic acid or sodium alginate as an solutionizer. Further, the inventive pharmaceutical composition may comprise anti-coagulating agent, lubricant, wetting agents, flavors, emulsifying agents and antiseptics.

In case of the parenteral formulation for administration, the composition of the present invention may be formulated into injections, creams, lotions, ointments, oils, humectants, gels, collyriums, aerosols and nasal inhalers by using the method known in the art.

Preferable sterilized injection agents may be one of non-toxic and parenterally acceptable solvents or suspensions. For pharmaceutically acceptable carrier and vehicle, there are saline, buffered saline, isotonic saline (for example, sodium phosphate monobasic, sodium phosphate dibasic, sodium chloride, potassium chloride, calcium chloride, and magnesium chloride or mixture thereof), linger solution, dextrose, water, sterilized water, glycerol, ethanol and mixture thereof. Preferably, as s solvent or suspension media, 1,3-butanediol and sterilized fixing oil are used. Fatty acids such as oleic acid may also be used for preparing injection agents.

A collyrium may be water-soluble ophthalmic solution, water-insoluble ophthalmic solution or ophthalmic emulsion. A collyrium of the present invention is prepared by dissolving or suspending a peptide of the present invention into a water-soluble solvent such as sterilized water or saline or a water-insoluble solvent such as plant oil of cottonseed oil or soybean oil. In this case, an isotonic agent, an pH regulating agent, a thickening agent, a suspending agent, an emulsifying agent, a preservative and similar additive to thereof which is pharmaceutically acceptable. In detail, the isotonic agent comprise sodium chloride, boric acid, sodium nitrate, potassium nitrate, D-mannotol and glucose. Specific examples of thickening agents comprise boric acid, anhydrous sodium sulfate, hydrochloric acid, citric acid, sodium citrate, nitric acid, potassium acetate, sodium carbonate and borax. Specific examples of pH regulating agents comprise methyl cellulose, hydroxypropylmethyl cellulose, polyvinyl alcohol, condroitin sodium sulfate and polyvinylpyrrolidone. Specific examples of suspending agents comprise polysorbate 80 and polyoxyethylene and hydrogenized castor oil. Specific examples of emulsifying agents comprise yolk lecithin and polysorbate 80, but not limited thereto. Specific examples of preservatives comprise benzalkonium chloride, benzethonium Chloride, chlorobutanol, phenylethyl alcohol and paraoxybenzoic acid ester but not limited thereto. The formulations are disclosed in Remington's Pharmaceutical Science, 15th Edition, 1975. Mack Publishing Company, Easton, Pa. 18042, Chapter 87: Blaug, Seymour.

Preferably, the pharmaceutical composition of the present invention may comprise 0.001~99.999 weight % and 99.999~0.0001 weight % of pharmaceutically acceptable carrier.

As used herein, the term amount refers to an amount delivering the drug to subject in need or showing effect against promotion of angiogenesis and effect on preventing or treating angiogenesis-related diseases in a subject and the refers to a mammal and, preferably, it refers to mammals comprising human and it may be cells, organs and tissues originated from animals. The subject may be a patient who needs treatment of diseases.

Total effective amount of a composition of the present invention may be administered to a patient with a single dose, or may be administered with multiple doses by fractionated treatment protocol. The pharmaceutical compositions of the present invention may contain variable amount of effective ingredient according to the disease severity. The total amount of a peptide of the present invention is preferably about 0.0001 ug to 500 mg/kg body weight/day, most preferably it may be 0.01 ug to 100 mg/kg body weight/day. However, the dose of the peptide may be suitably determined by considering various factors, such as age, body weight, health condition, sex, disease severity, diet and excretion of a subject in need of treatment, as well as administration time and administration route. Therefore, when those are considered, skilled person in the art may determine appropriate dose of the composition for a certain use. A pharmaceutical composition of the present invention may not limit formulations, administration routes, and administration methods as long as they show the effect of the present invention.

Advantageous Effects

As can be seen from the foregoing, the present invention provides a novel peptide, a composition for promoting angiogenesis comprising the peptide as an active ingredient. The peptide of the present invention has an excellent effect on promoting angiogenesis and a pharmaceutical composition of the present invention has superior effect of promoting angiogenesis than VEGF, and because of far lower molecular weight, it is easier penetrate into blood vessels and tissues compared to VEGF. Accordingly, a composition comprising the peptide is useful for preventing and/or treating angiogenesis-related diseases and for preparing regeneration of skin flap, wound and burn healing, implantation of artificial skin and preparation of blood vessels for transplantation.

MODE FOR INVENTION

Hereafter, the present invention will be described in detail by the examples. It is to be understood, however, that these examples are for illustrative purpose only and are not constructed to limit the scope of the present invention.

Example 1

Preparation of Peptide

Peptides having amino acid sequences described in Table 1 were synthesized using an automated peptide synthesizer (Milligen 9050, Millipore, USA) and then purely isolated by C18 reversed-phase high-performance liquid chromatography (HPLC) (Waters Associates, USA). ACQUITY UPLC BEH300 C18 column (2.1×100 mm, 1.7 μm, Waters Co, USA) was used.

TABLE 1

Amino acid sequence of prepared peptides

| SEQ ID NO. | Peptide name | Sequence |
|---|---|---|
| 1 | Pep__1 | AGES |
| 2 | Pep__2 | PKAGES |
| 3 | Pep__3 | KNAGDS |
| 4 | Pep__4 | KNAGHS |
| 5 | Pep__5 | RQAGDS |
| 6 | Pep__6 | RQAGHS |
| 7 | Pep__11 | AGESQK |

Example 2

Effect on Proliferation of HUVECs

In order to investigate the effect of the 7 peptides prepared in Example 1 on blood vessel formation, human umbilical vein endothelial cells (HUVECs) were treated with the peptide of the present invention and their proliferation was observed.

HUVECs were cultured in endothelial cell basal medium-2 (EBM-2, Clonetics Co., San Diego, USA) containing 2% fetal bovine serum (FBS). The cultured HUVECs were transferred to a 96-well plate, with 1000 cells per each well. After culturing for 24 hours followed by addition of the 7 peptides of the peptide of the present invention to each well, they were further cultured for 48 hours. The cells treated with VEGF instead of the peptide of the present invention and those treated with nothing were cultured under the same condition, as positive control group and negative control group, respectively. Upon completion of the culturing, the degree of cell proliferation was measured using the CyQUANT kit (Invitrogen, USA).

Figure 1:
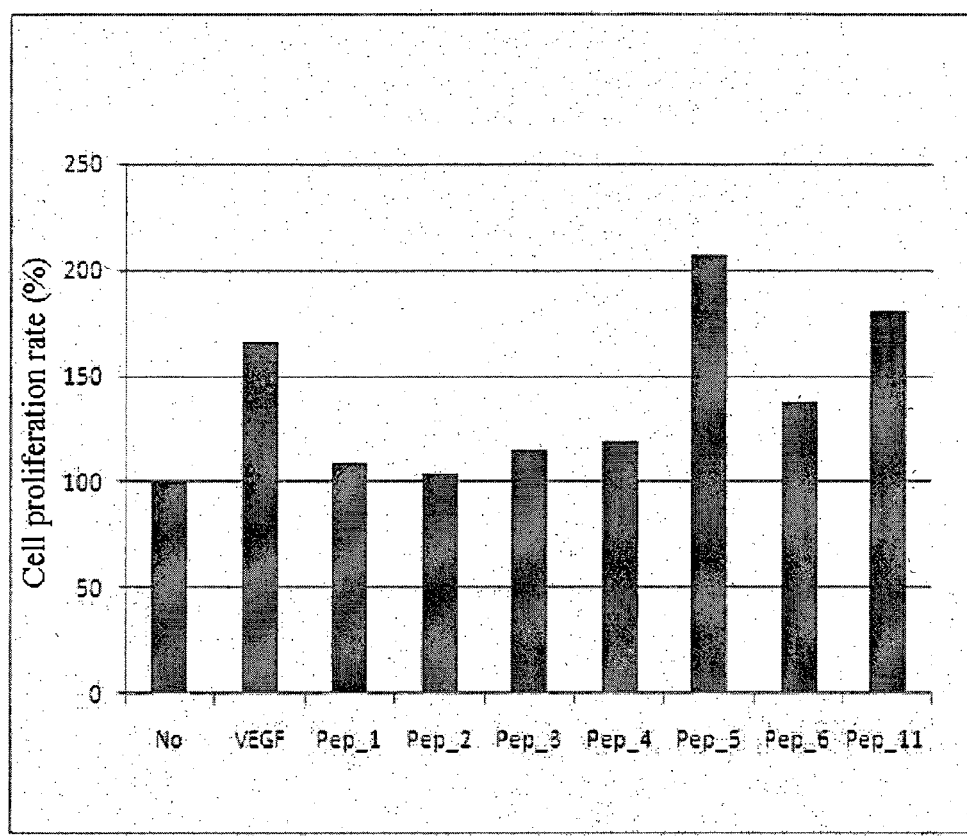
FIG. 1 compares the effect of the peptide of the present invention on promotion of proliferation of endothelial cells (ECs) (No: negative control, VEGF: positive control, Pep__1 to 6 and Pep__11: peptides of SEQ ID NOS. 1 to 7)

As seen from Table 2 and FIG. 1, the peptides of the present invention exhibited superior effect of promoting proliferation of the HUVECs. Some peptides showed even better result than the positive control VEGF.

TABLE 2

Effect of promoting cell proliferation

| Peptide/control group | Cell proliferation (%) |
|---|---|
| Negative control (untreated) | 100 |
| Positive control (VEGF) | 166.0 |
| Pep_1 | 109.6 |
| Pep_2 | 104.4 |
| Pep_3 | 115.7 |
| Pep_4 | 119.6 |
| Pep_5 | 207.5 |
| Pep_6 | 138.0 |
| Pep_11 | 146.5 |

Example 3

Effect on Migration of HUVECs

In order to investigate the effect of the 7 peptides prepared in Example 1 on blood vessel formation, migration of HUVECs was measured.

The bottom portion of a chamber of a 24-well plate (Corning Costar, USA) having a polycarbonate filter with pores therebelow was coated with 0.5 mg/mL collagen type 1 (10 mL). After adding EBM-2 containing the 7 peptides of the peptide of the present invention to the bottom portion of the chamber, HUVECs were inoculated at the upper portion of the chamber, with $1 \times 10^5$ cells per well. After incubation at 37° C. for 10 hours, the cells that had passed through the polycarbonate filter were fixed with methanol, stained with hematoxylin, and counted under a microscope.

Figure 2:
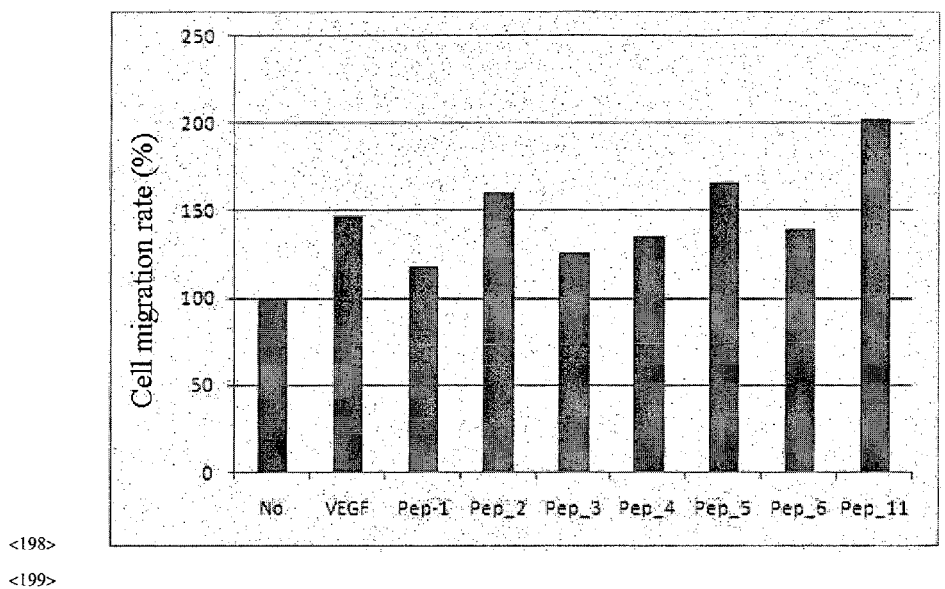
FIG. 2 compares the effect of the peptide of the present invention on promotion of migration of ECs (No: negative control, VEGF: positive control, Pep__1 to 6 and Pep__11: peptides of SEQ ID NOS. 1 to 7)

As seen from Table 3 and FIG. 2, the peptides of the present invention promoted migration of the HUVECs. Some peptides showed even better result than the positive control VEGF.

TABLE 3

Effect of promoting cell migration

| Peptide/control group | Cell migration (%) |
|---|---|
| Negative control (untreated) | 100 |
| Positive control (VEGF) | 146.3 |
| Pep_1 | 118.0 |
| Pep_2 | 159.5 |
| Pep_3 | 125.8 |
| Pep_4 | 135.5 |
| Pep_5 | 165.4 |

TABLE 3-continued

Effect of promoting cell migration

| Peptide/control group | Cell migration (%) |
|---|---|
| Pep_6 | 138.6 |
| Pep_11 | 202.2 |

Example 4

Effect on Promotion of Tube Formation of HUVECs

The effect of the peptide of the present invention on tube formation of HUVECs was investigated.

HUVECs were cultured in EGM-2 containing 2% FBS and then starved for 12 hours in an FBS-free medium. Matrigel (BD Biosciences, USA) was uniformly applied and hardened on a 24-well plate, 150 μL per each, taking cautions to avoid bubbles. After suspending the cells in a mixture of the peptide of the present invention with a medium containing 1% FBS, the cells were inoculated, with $1 \times 10^5$ cells per each well, and incubated at 37° C. 18 hours later, it was observed under a microscope whether the HUVECs form tubes.

Figure 3:
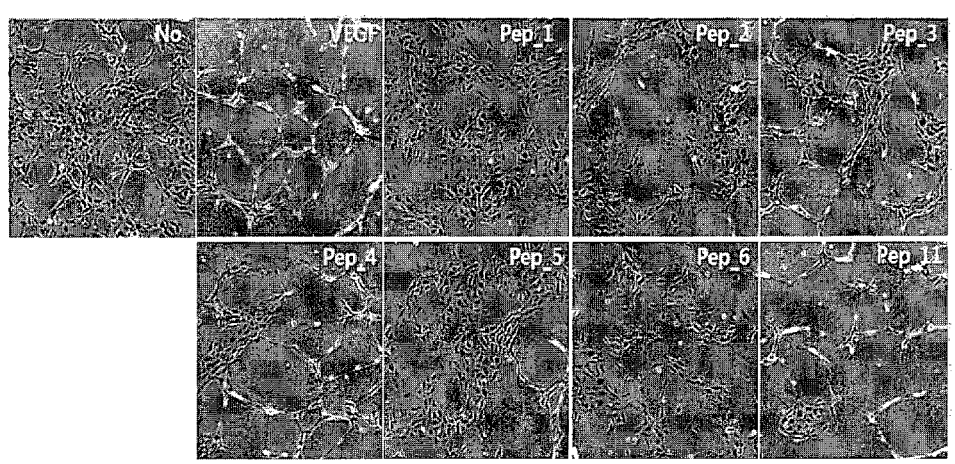
FIG. 3 shows photographic images showing that tube formation of ECs is promoted by the peptide of the present invention (No: negative control, VEGF: positive control, Pep__1 to 6 and Pep__11: peptides of SEQ ID NOS. 1 to 7).

As seen from FIG. 3, it was confirmed that the peptides of the present invention promote the tube formation of the HUVECs.

Example 5

Effect on Promotion of Blood Vessel Formation

The angiogenesis-promoting ability of the peptide of the present invention was investigated by in vivo Matrigel plug assay.

600 μL of a mixture of each of the peptides of the present invention with growth factor-reduced Matrigel (BD Biosciences, USA) was subcutaneously injected to a 7-week-old male C57BL/6 mouse. As a positive control group, VEGF (R&D Systems, USA) known to induce angiogenesis was injected to the mouse. After 1 week, the mouse was sacrificed and the hardened Matrigel plug was taken out, and the degree of blood vessel formation was quantified. The quantification was carried out by measuring the amount of hemoglobin using the Drabkin's reagent kit (Sigma, USA).

As a result, it was confirmed that the injection of the peptide of the present invention exhibited remarkably superior angiogenesis as compared to the control group.

INDUSTRIAL APPLICABILITY

The novel peptide of the present invention has an excellent effect on promoting angiogenesis. The peptide of the present invention has superior effect of promoting angiogenesis than VEGF, and because of far lower molecular weight, it is easier penetrate into blood vessels and tissues compared to VEGF. Accordingly, a composition comprising the peptide is useful for preventing and/or treating angiogenesis-related diseases and for preparing regeneration of skin flap, wound and burn healing, implantation of artificial skin and preparation of blood vessels for transplantation.

The invention claimed is:

1. An isolated peptide, consisting of the amino acid sequence represented by SEQ ID NO: 7, wherein the amino acid sequence is optionally amidated.

2. A composition comprising the peptide of claim 1.

3. The isolated peptide of claim 1, wherein the peptide is amidated.

* * * * *

SEQUENCE LISTING

<160> NUMBER OF SEQ ID NOS: 7

<210> SEQ ID NO 1
<211> LENGTH: 4

```
<212> TYPE: PRT
<213> ORGANISM: Artificial Sequence
<220> FEATURE:
<223> OTHER INFORMATION: Pep_1 : Artificial Peptide for Promotion of
      Angiogenesis

<400> SEQUENCE: 1

Ala Gly Glu Ser
  1

<210> SEQ ID NO 2
<211> LENGTH: 6
<212> TYPE: PRT
<213> ORGANISM: Artificial Sequence
<220> FEATURE:
<223> OTHER INFORMATION: Pep_2 : Artificial Peptide for Promotion of
      Angiogenesis

<400> SEQUENCE: 2

Pro Lys Ala Gly Glu Ser
  1               5

<210> SEQ ID NO 3
<211> LENGTH: 6
<212> TYPE: PRT
<213> ORGANISM: Artificial Sequence
<220> FEATURE:
<223> OTHER INFORMATION: Pep_3 : Artificial Peptide for Promotion of
      Angiogenesis

<400> SEQUENCE: 3

Lys Asn Ala Gly Asp Ser
  1               5

<210> SEQ ID NO 4
<211> LENGTH: 6
<212> TYPE: PRT
<213> ORGANISM: Artificial Sequence
<220> FEATURE:
<223> OTHER INFORMATION: Pep_4 : Artificial Peptide for Promotion of
      Angiogenesis

<400> SEQUENCE: 4

Lys Asn Ala Gly His Ser
  1               5

<210> SEQ ID NO 5
<211> LENGTH: 6
<212> TYPE: PRT
<213> ORGANISM: Artificial Sequence
<220> FEATURE:
<223> OTHER INFORMATION: Pep_5 : Artificial Peptide for Promotion of
      Angiogenesis

<400> SEQUENCE: 5

Arg Gln Ala Gly Asp Ser
  1               5

<210> SEQ ID NO 6
<211> LENGTH: 6
<212> TYPE: PRT
<213> ORGANISM: Artificial Sequence
<220> FEATURE:
<223> OTHER INFORMATION: Pep_6 : Artificial Peptide for Promotion of
      Angiogenesis

<400> SEQUENCE: 6

Arg Gln Ala Gly His Ser
```

```
                    1               5

<210> SEQ ID NO 7
<211> LENGTH: 6
<212> TYPE: PRT
<213> ORGANISM: Artificial Sequence
<220> FEATURE:
<223> OTHER INFORMATION: Pep_11 : Artificial Peptide for Promotion of
      Angiogenesis

<400> SEQUENCE: 7

Ala Gly Glu Ser Gln Lys
  1               5
```